US012005049B2

(12) United States Patent
Matsuda et al.

(10) Patent No.: US 12,005,049 B2
(45) Date of Patent: Jun. 11, 2024

(54) METHODS OF PREVENTING CANCER METASTASIS

(71) Applicants: MediciNova, Inc., La Jolla, CA (US); The Trustees of Columbia University in the City of New York, New York, NY (US)

(72) Inventors: Kazuko Matsuda, La Jolla, CA (US); Grazia Ambrosini, Astoria, NY (US); Gary K. Schwartz, Briarcliff Manor, NY (US); Alex J. Rai, Montclair, NJ (US)

(73) Assignees: MediciNova, Inc., La Jolla, CA (US); The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 17/872,855

(22) Filed: Jul. 25, 2022

(65) Prior Publication Data
US 2023/0037014 A1    Feb. 2, 2023

Related U.S. Application Data

(60) Provisional application No. 63/225,820, filed on Jul. 26, 2021.

(51) Int. Cl.
*A61K 31/437*    (2006.01)
*A61P 35/00*    (2006.01)

(52) U.S. Cl.
CPC ............ *A61K 31/437* (2013.01); *A61P 35/00* (2018.01)

(58) Field of Classification Search
CPC .............................. A61K 31/437; A61P 35/00
See application file for complete search history.

(56) References Cited

U.S. PATENT DOCUMENTS

| | | | |
|---|---|---|---|
| 6,395,747 B1 | 5/2002 | Sakoda et al. | |
| 8,138,201 B2 | 3/2012 | Kalafer et al. | |
| 8,338,453 B2 | 12/2012 | Kalafer et al. | |
| 9,114,136 B2 | 8/2015 | Kalafer et al. | |
| 9,314,452 B2 | 4/2016 | Kalafer et al. | |
| 10,258,611 B2 | 4/2019 | Matsuda et al. | |
| 10,391,085 B2 | 8/2019 | Matsuda et al. | |
| 10,744,123 B2 | 8/2020 | Matsuda et al. | |
| 10,946,071 B2 | 3/2021 | Matsuda | |
| 11,083,713 B2 | 8/2021 | Kalafer et al. | |
| 11,154,540 B2 | 10/2021 | Matsuda | |
| 11,278,531 B2 | 3/2022 | Matsuda et al. | |
| 11,446,283 B2 | 9/2022 | Matsuda et al. | |
| 2006/0160843 A1 | 7/2006 | Johnson et al. | |
| 2015/0011581 A1 | 1/2015 | Kalafer et al. | |
| 2015/0157584 A1* | 6/2015 | Guan ................. | A61K 31/661 435/375 |
| 2017/0014390 A1 | 1/2017 | Kalafer et al. | |
| 2017/0020851 A1 | 1/2017 | Kalafer et al. | |
| 2019/0247369 A1 | 8/2019 | Matsuda | |
| 2020/0030301 A1 | 1/2020 | Matsuda et al. | |
| 2020/0038382 A1 | 2/2020 | Matsuda et al. | |
| 2021/0085613 A1 | 3/2021 | Matsuda et al. | |
| 2021/0177812 A1 | 6/2021 | Matsuda | |
| 2021/0308109 A1 | 10/2021 | Iwaki et al. | |
| 2022/0168283 A1 | 6/2022 | Kalafer et al. | |
| 2022/0241252 A1 | 8/2022 | Matsuda et al. | |
| 2023/0037014 A1 | 2/2023 | Matsuda et al. | |
| 2023/0090534 A1 | 3/2023 | Kazuko et al. | |
| 2023/0116096 A1 | 4/2023 | Matsuda et al. | |
| 2023/0285367 A1 | 9/2023 | Matsuda | |

OTHER PUBLICATIONS

Cho, et al., "Allosteric Inhibition of Macrophage Migration Inhibitory Factor Revealed by Ibudilast," *PNAS*, vol. 107, No. 25, pp. 11313-11318 (2010).
Gibson et al., "The Inhibitory Profile of Ibudilast Against the Human Phosphodiesterase Enzyme Family," European Journal of Pharmacology, vol. 538, pp. 39-42 (2006).
Sanftner et al., "Cross-species comparisons of the pharmacokinetics of ibudilast," Xenobiotica, vol. 39, No. 12, pp. 964-977 (Nov. 2009). [Abstract].
Obernolte, R., et al. (1993) "The cDNA of a human lymphocyte cyclic-AMP phosphodiesterase (PDE IV) reveals a multigene family" Gene 129: 239-247.
Rile et al., "Potentiation of Ibudilast Inhibition of Platelet Aggregation in the Presence of Endothelial Cells," Thrombosis Research, 102 239-246 (2001). [Abstract].
Souness et al., "Possible Role of Cyclic AMP Phosphodiesterases in the Actions of Ibudilast on Eosinophil Thromboxane Generation and Airways Smooth Muscle Tone," British Journal of Pharmacology, 111:1081-1088 (1994).
Suzumura et al., "Ibudilast suppresses TNF.alpha. production by glial cells functioning mainly as type III phosphodiesterase inhibitor in NCS," Brain Research, 837:203-212 (1999).
Takuma et al., "Ibudilast attenuates actrocyte apoptsis via cyclic GMP signaling pathway in an in vitro reperfusion model," British Journal of Pharmacology, 133:841-848 (2001).
Jeffery et al., "The preparation and characterization of poly(lactide-co-glycolide) microparticles. II. The Entrapment of a Model Protein Using a (water-in-oil)-in-water Emulsion Solvent Evaporation Technique," Pharm. Research, vol. 10, pp. 362-368 (1993).
Yang, et al., "The Emerging Role of Toll-Like Receptor 4 in Myocardial Inflammation," *Cell Death and Disease*, vol. 7, e2234, 10 pages (2016).
Surriga et al., "Crizotinib, a c-Met Inhibitor, Prevents Metastasis in a Metastatic Uveal Melanoma Model," Molecular Cancer Therapies, vol. 12, pp. 2817-2826 (2013).

(Continued)

*Primary Examiner* — Bruck Kifle
(74) *Attorney, Agent, or Firm* — Foley & Lardner LLP

(57) ABSTRACT

A method of preventing metastasis of a cancer in a patient in need thereof includes administering to the patient a therapeutically effective amount of ibudilast, or a pharmaceutical salt thereof.

16 Claims, 3 Drawing Sheets

(56) References Cited

OTHER PUBLICATIONS

International Search Report and Written Opinion issued in International Patent Application No. PCT/US2022/038157, dated Oct. 10, 2022.

Carvajal, et al., "Metastatic Disease form Uveal Melanoma: Treatment Options and Future Prospects," *British Journ. of Ophthalmology*, vol. 101, No. 1, pp. 38-44 (Aug. 2016).

Singh, et al., "Uveal Melanoma: A Review of the Literature," *Oncology and Therapy*, vol. 6, No. 1, pp. 87-104 (Jun. 2018).

Schulz, et al., "Microenvironmental Regulation of Tumor Progression and Therapeutic Response in Brain Metastasis," *Frontiers in Immunology*, vol. 10, p. 1713 (Jul. 2019).

Rolan, et al., "Ibudilast: a Review of its Pharmacology, Efficacy and Safety in Respiratory and Neurological Disease," *Expert Opinion Pharmacotherapy*, vol. 10, No. 17, pp. 2897-2904 (Dec. 2009).

\* cited by examiner

METHODS OF PREVENTING CANCER METASTASIS

CROSS REFERENCE TO RELATED APPLICATIONS

This application claims the benefit of priority to U.S. Provisional Patent Application No. 63/225,820, filed Jul. 26, 2021, and which is incorporated herein by reference in its entirety.

BACKGROUND

Ibudilast has been widely used in Japan for relieving symptoms associated with ischemic stroke or bronchial asthma. In recent clinical trials, its use in the treatment of multiple sclerosis (MS), an inflammatory disease of the central nervous system, has been explored (News.Medical.Net; Pharmaceutical News, 2 Aug. 2005), As disclosed in this publication, this clinical trial was expected to treat "relapsing-remitting MS." however, no mention is made of progressive multiple sclerosis. In U.S. Pat. No. 6,395,747, ibudilast is disclosed as a treatment for multiple sclerosis, which is generally understood to mean relapsing and remitting multiple sclerosis, not progressive multiple sclerosis. U.S. Patent Application Publication No. 20060160843 discloses ibudilast for the treatment of intermittent and short term pain, however, this is not pain related to a progressive neurodegenerative disease. However, U.S. Pat. No. 9,314,452 discloses ibudilast as a treatment for amyotrophic lateral sclerosis, a progressive neurodegenerative disease. Similarly. U.S. Pat. No. 8,138,201 discloses ibudilast as a treatment for primary progressive multiple sclerosis and/or secondary progressive multiple sclerosis.

While the use of ibudilast for a number of varying indications has been reported to date, to the best of the inventors' knowledge, its use in preventing cancer metastasis in patients has heretofore remained largely unexplored.

SUMMARY

Disclosed herein in one aspect are methods of preventing metastasis of a cancer in a patient in need thereof, the methods comprising administering to the patient a therapeutically effective amount of ibudilast, or a pharmaceutical salt thereof.

Disclosed herein in another aspect are methods of ameliorating metastasis of a cancer in a patient in need thereof, the methods comprising administering to the patient a therapeutically effective amount of ibudilast, or a pharmaceutical salt thereof.

Disclosed herein in another aspect are methods of minimizing metastasis of a cancer in a patient in need thereof, the methods comprising administering to the patient a therapeutically effective amount of ibudilast, or a pharmaceutical salt thereof.

In some embodiments, ibudilast is administered in combination with one or more additional active agents. In some embodiments, the one or more additional active agents are selected from the group consisting of chemotherapy, immunotherapy, epigenetic therapy, or liver-directed therapy. In some embodiments, the one or more additional active agents are selected from the group consisting of ICON-1; AU-011; dacarbazine; interferon-α; temozolomide; cisplatin; tamoxifen; treosulfan; fotemustine; crizotinib; ipilimumab; tremelimumab; nivolumab; pernbrolizumab; atezolizumab; IMCgp100; glembatumumab; selumetinib; trametinib; sotrastaurin; LXS196; AEB071; BYL719; binimetinib; sunitinib; cabozantinib; sorafenib; carboplatin; paclitaxel; valproic acid; vorinostat; PLX51107; tumor infiltrating lymphocytes; glembatumumab vedontin; and entinostat. In some embodiments, ibudilast is administered in combination with one or more selected from the group consisting of surgery, brachytherapy, charged-particle radiotherapy, laser therapy, photodynamic therapy, radiofrequency ablation, stereotactic radiotherapy, hepatic intra-arterial infusion, isolated hepatic perfusion, percutaneous hepatic perfusion, and prophylactic liver radiotherapy. In some embodiments, ibudilast is administered to the patient as adjuvant therapy. In some embodiments, the cancer is: a cancer of the circulatory system selected from angiosarcoma, fibrosarcoma, rhabdomyosarcoma, liposarcoma, myxoma, rhabdomyoma, fibroma, lipoma and teratoma, cancer of the mediastinum and pleura, or a vascular tumor; a cancer of the respiratory tract selected from cancer of the nasal cavity and middle ear, cancer of accessory sinuses, cancer of larynx, cancer of the trachea, cancer of the bronchus and lung, small cell lung cancer (SCLC), non-small cell lung cancer (NSCLC), bronchogenic carcinoma, squamous cell carcinoma, undifferentiated small cell carcinoma, undifferentiated large cell carcinoma, adenocarcinoma, alveolar (bronchiolar) carcinoma, bronchial adenoma, sarcoma, lymphoma, chondromatous hamartoma, or mesothelioma; a cancer of the gastrointestinal system selected from squamous cell carcinoma, adenocarcinoma, leiomyosarcoma, lymphoma, carcinoma, leiomyosarcoma, ductal adenocarcinoma, insulinoma, glucagonoma, gastrinoma, carcinoid tumors, vipomal, adenocarcinoma, carcinoid tumors, Karposi's sarcoma, leiomyoma, hemangioma, lipoma, neurofibroma, fibroma, adenocarcinoma, tubular adenoma, villous adenoma, hamartoma, or leiomyoma; a cancer of the genitourinary tract selected from adenocarcinoma, Wilm's tumor (nephroblastoma), lymphoma, leukemia, squamous cell carcinoma, transitional cell carcinoma, adenocarcinoma, adenocarcinoma, sarcoma of the prostate, seminoma, teratoma, embryonal carcinoma, teratocarcinoma, choriocarcinoma, interstitial cell carcinoma, fibroma, fibroadenoma, adenomatoid tumors, or lipoma; a cancer of the liver selected from hepatoma (hepatocellular carcinoma), cholangiocarcinoma, hepatoblastoma, angiosarcoma, hepatocellular adenoma, hemangioma, pheochromocytoma, insulinoma, vasoactive intestinal peptide tumor, islet cell tumor, or glucagonoma; a cancer of the bone selected from osteogenic sarcoma (osteosarcoma), fibrosarcoma, malignant fibrous histiocytoma, chondrosarcoma, Ewing's sarcoma, malignant lymphoma (reticulum cull sarcoma), multiple myeloma, malignant giant cell tumor chordoma, osteochronfroma (osteocartilaginous exostoses), benign chondroma, chondroblastoma, chondromyxofibroma, osteoid osteoma, or giant cell tumors; a cancer of the nervous system selected from primary CNS lymphoma, osteoma, hemangioma, granuloma, xanthoma, osteitis deformans, meningioma, meningiosarcoma, gliomatosis, astrocytoma, medulloblastoma, glioma, ependymoma, germinoma. (pinealoma), oligodendroglioma, schwannoma, retinoblastoma, congenital tumors, spinal cord neurofibroma, meningioma, glioma, or sarcoma; a cancer of the reproductive system selected from endometrial carcinoma, cervical carcinoma, pre-tumor cervical dysplasia, ovarian carcinoma, serous cystadenocarcinoma, mucinous cystadenocarcinoma, unclassified carcinoma, granulosa-thecal cell tumors, Sertoli-Leydig cell tumors, dysgerminoma, malignant teratoma, squamous cell carcinoma of the vulva, intraepithelial carcinoma of the vulva, adenocarcinoma of the vulva, fibrosarcoma of the vulva, melanoma of the vulva, vaginal clear cell carcinoma, vaginal squamous cell carcinoma, vaginal botryoid sarcoma (embryonal rhabdomyosarcoma), carcinoma of the fallopian tubes placental cancer, penile cancer, prostate cancer, or testicular cancer; a cancer of the hematologic system selected from myeloid, acute lymphoblastic leukemia, chronic lymphocytic leukemia, myeloproliferative diseases, multiple myeloma, myelodysplastic syndrome, Hodgkin's disease, or non-Hodgkin's lymphoma; a cancer of the oral cavity selected from lip cancer, tongue cancer, gum cancer, floor of mouth cancer, palate cancer, parotid gland cancer, salivary gland cancer, tonsil cancer, cancer of the oropharynx, cancer of the nasopharynx, pyriform sinus cancer, or cancer of the hypopharynx; a cancer of the skin selected from malignant melanoma, cutaneous melanoma, basal cell carcinoma, squamous cell carcinoma, Karposi's sarcoma, moles dysplastic nevi, lipoma, angioma, dermatofibroma, or keloidal cancer; or a cancer selected from cancer of the adrenal glands, neuroblastoma, cancer of connective and soft tissue, cancer of the retroperitoneum and peritoneum, eye cancer, intraocular melanoma, cancer of adnexa, breast cancer, head or/and neck cancer, anal cancer, thyroid cancer, parathyroid cancer, cancer of the adrenal gland, cancer of the endocrine glands and related structures, secondary and unspecified malignant neoplasm of lymph nodes, secondary malignant neoplasm of respiratory and digestive systems, or secondary malignant neoplasm of other sites. In some embodiments, the cancer is eye cancer. In some embodiments, the eye cancer is uveal melanoma. In some embodiments, ibudilast, or the pharmaceutically acceptable salt thereof, is administered for at least 3 months. In some embodiments, ibudilast, or the pharmaceutically acceptable salt thereof, is administered for at least six months. In some embodiments, ibudilast, or the pharmaceutically acceptable salt thereof, is administered for at least one year. In some embodiments, ibudilast, or the pharmaceutically acceptable salt thereof, is administered for at least two years. In some embodiments, ibudilast, or the pharmaceutically acceptable salt thereof, is administered at least once daily. In some embodiments, ibudilast, or the pharmaceutically acceptable salt thereof, is administered orally. In some embodiments, the therapeutically effective amount of ibudilast, or the pharmaceutically acceptable salt thereof, is from 0.1 mg to 720 mg per day. In some embodiments, the therapeutically effective amount of ibudilast, or the pharmaceutically acceptable salt thereof is at least 30 mg/day. In some embodiments, the therapeutically effective amount of ibudilast, or the pharmaceutically acceptable salt thereof, is from 30 mg to 200 mg per day. In some embodiments, the therapeutically effective amount of ibudilast, or the pharmaceutically acceptable salt thereof, is 60 mg to 600 mg daily. In some embodiments, the therapeutically effective amount of ibudilast, or the pharmaceutically acceptable salt thereof, is 100 mg to 480 mg daily. In some embodiments, the therapeutically effective amount of ibudilast, or the pharmaceutically acceptable salt thereof, is selected from the group consisting of 30 mg/day, 60 mg/day, 90 mg/day, 100 mg/day, 120 mg/day, 150 mg/day, 180 mg/day, 210 mg/day, 240 mg/day, 270 mg/day, 300 mg/day, 360 mg/day, 400 mg/day, 440 mg/day, 480 mg/day, 520 mg/day, 580 mg/day, 600 mg/day, 620 mg/day, 640 mg/day, 680 mg/day, and 720 mg/day. In some embodiments, the therapeutically effective amount is administered as a single dose or is divided into two, three, or four doses. In some embodiments, ibudilast is administered continually.

DETAILED DESCRIPTION

Figure 1A:
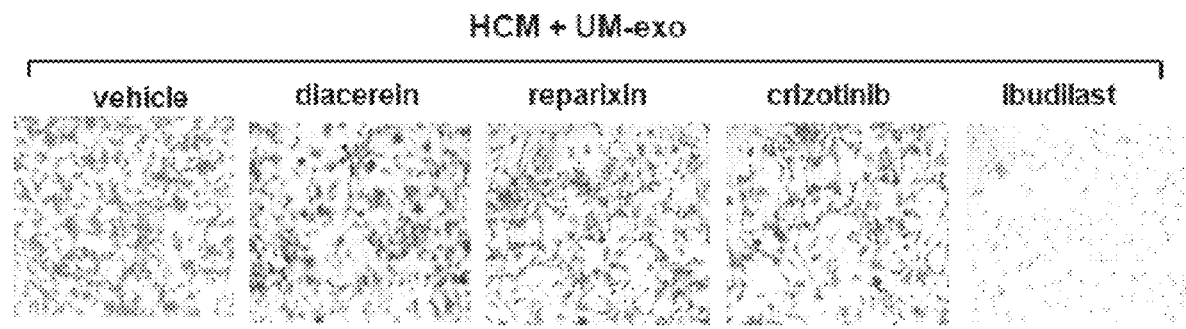
FIG. 1A depicts trans-well migration assay results in which Omm1.3 cells were stimulated with hepatocyte conditioned media and uveal melanoma exosomes (HCM+UM-exo) in the presence of vehicle (DMSO), 10 µM diacerein, 1.0 µM reparixin, 0.25 µM crizotinib or 25 µM ibudilast.

The practice of the present disclosure will employ, unless otherwise indicated, conventional methods of chemistry, biochemistry, and pharmacology, within the skill of the art. Such techniques are explained fully in the literature. See, e.g.; A. L. Lehninger, Biochemistry (Worth Publishers, Inc., current addition); Morrison and Boyd, Organic Chemistry (Allyn and Bacon, Inc., current addition); J. March, Advanced Organic Chemistry (McGraw Hill, current addition); Remington: The Science and Practice of Pharmacy, A. Gennaro, Ed., 20th Ed.; FDA's Orange Book, Goodman & Gilman The Pharmacological Basis of Therapeutics, J. Griffith Hardman, L. L. Limbird, A. Gilman, 11th Ed., 2005, The Merck Manual, 18th edition, 2007, and The Merck Manual of Medical Information 2003.

All publications cited herein, including internet articles, the FDA Orange Book (available on the FDA's website), hooks, handbooks, journal articles, patents and patent applications, whether supra or infra, are hereby incorporated by reference in their entirety.

Definitions

Before describing the present disclosure in detail, it is to be understood that this disclosure is not limited to particular administration modes, patient populations, and the like, as such may vary, as will be apparent from the accompanying description.

It must be noted that, as used in this specification and the intended claims, the singular forms "a," "an," and "the" include plural referents unless the context clearly dictates otherwise. Thus, for example, reference to "a drug" includes a single drug as well as two or more of the same or different drugs, reference to "an optional excipient" refers to a single optional excipient as well as two or more of the same or different optional excipients, and the like.

In describing and claiming the present disclosure, the following terminology will be used in accordance with the definitions described below.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention. When an embodiment is defined by one of these terms (e.g., "comprising") it should be understood that this disclosure also includes alternative embodiments, such as "consisting essentially of" and "consisting of" for said embodiment.

"Pharmaceutically acceptable excipient or carrier" refers to an excipient that may optionally be included in the compositions of the disclosure and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethyl succinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

"Active molecule" or "active agent" as described herein includes any agent, drug, compound, composition of matter or mixture which provides some pharmacologic, often beneficial, effect that can be demonstrated in vivo or in vitro. This includes foods, food supplements, nutrients, nutraceuticals, drugs, vaccines, antibodies, vitamins, and other beneficial agents. As used herein, the terms further include any physiologically or pharmacologically active substance that produces a localized or systemic effect in a patient. In specific embodiments, the active molecule or active agent may include ibudilast or a pharmaceutically acceptable salt thereof.

"Substantially" or "essentially" means nearly totally or completely, for instance, 95% or greater of some given quantity.

"Optional" or "optionally" means that the subsequently described circumstance may or may not occur, so that the description includes instances where the circumstance occurs and instances where it does not.

The terms "subject," "individual" or "patient" are used interchangeably herein and refer to a vertebrate, preferably a mammal. Mammals include, but are not limited to, mice, rodents, rats, simians, humans, farm animals, dogs, cats, sport animals and pets.

The terms "pharmacologically effective amount" or "therapeutically effective amount" of a composition or agent, as provided herein, refer to a nontoxic but sufficient amount of the composition or agent to provide the desired response, such as prevention of cancer metastasis. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

The term "preventing metastasis of a cancer" as used herein includes one or moreof treating, ameliorating, and minimizing cancer metastasis in the patient. In some embodiments, the preventing leads to absence of cancer metastasis in the patient. In some embodiments, the preventing leads to minimization of cancer metastasis in the patient. In some embodiments, the preventing leads to absence or minimization of cancer metastasis in the patient.

The term "about," will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term. For example, in some embodiments, it will mean plus or minus 5% of the particular term. Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

The methods of the disclosure are based upon administration of the molecule, ibudilast. Ibudilast is a small molecule drug (molecular weight of 230.3) having the structure shown below.

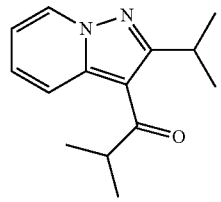 [SMILES: CC(C)C(=O)c1c(C(C)C)nn2ccccc12]

Ibudilast is also found under ChemBank ID 3227, CAS #50847-11-5, and Beilstein Handbook Reference No. 5-24-03-00396, Its molecular formula corresponds to $C_{14}H_{18}N_2O$. Ibudilast is also known by various chemical names including 2-methyl-1-(2-(1-methylethyl)pyrazolo(1,5-a)pyridin-3-yl)1-propanone; 3-isobutyryl-2-isopropylpyrazolo(1,5-a)pyridine, and 1-(2-isopropyl-pyrazolo[1,5-a]pyridin-3-yl)-2-methyl-propan-1-one. Other synonyms for ibudilast include Ibudilastum (Latin), BRN 0656579, KC-404, and MN-166. Its brand name is Ketas®. Ibudilast, as referred to herein, is meant to include any and all pharmaceutically acceptable salt forms thereof, prodrug forms (e.g., the corresponding ketal, oxime, oxime derivative, hydrazone, or semicarbazone), solvates, and the like, as appropriate for use in its intended formulation for administration.

Ibudilast is also a selective inhibitor of cyclic nucleotide phosphodiesterases (PDEs) 3A, 4, 10A1 and 11A1 (Gibson et at, Eur J Pharmacol 538: 39-42, 2006), has toll-like receptor-4 (TLR4) antagonistic activity (Yang et al., Cell Death and Disease (2016) 7, e2234; doi:10.1038/cddis.2016.140) and has also been reported to have leukotriene D4 and PAF antagonistic activities. Its profile appears effectively anti-inflammatory and unique in comparison to other PDE inhibitors and anti-inflammatory agents. PDEs catalyze the hydrolysis of the phosphoester bond on the 3-carbon to yield the corresponding 5'-nucleotide monophosphate. Thus, they regulate the cellular concentrations of cyclic nucleotides. Since extracellular receptors for many hormones and neurotransmitters utilize cyclic nucleotides as second messengers, the PDEs also regulate cellular responses to these extracellular signals. There are at least eight classes of PDEs: $Ca^{2+}$/calmodulin-dependent (PDE1), cGMP-stimulated PDEs (PDE2); cGMP-inhibited PDEs (PDE3); cAMP-specific PDEs (PDE4); cGMP-binding PDEs (PDES); photoreceptor PDEs (PDE6); high affinity, cAMP-specific PDEs (PDE7); and high affinity cGMP-specific PDEs (PDE9). Ibudilast acts to suppress inflammation via action on inflammatory cells (e.g., glial cells) resulting in the suppression of both pro-inflammatory mediator and neuroactive mediator release. Ibudilast may also suppress the production of pro-inflammatory cytokines (IL-1β, TNF-α) and may enhance the production of the anti-inflammatory cytokines (IL-4, IL-10). References related to the foregoing include the following: Obernolte, R., et al. (1993) "The cDNA of a human lymphocyte cyclic AMP phosphodiesterase (PDE IV) reveals a multigene family" Gene 129: 239-247; Rile, G. et al. (2001) "Potentiation of ibudilast inhibition of platelet aggregation in the presence of endothelial cells" Thromb. Res. 102: 239-246; Souness, J. E., et al. (1994) "Possible role of cyclic AMP phosphodiesterases in the actions of ibudilast on eosinophil thromboxane generation and airways smooth muscle tone" Br. J. Pharmacol. 111: 1081-1088; Suzumura, A., et al. (1999) "Ibudilast suppresses TNF alpha production by glial cells functioning mainly as type HI phosphodiesterase inhibitor in CNS" Brain Res. 837: 203-212; Takuma, K., et al. (2001) "Ibudilast attenuates astrocyte apoptosis via cyclic GMP signaling pathway in an in vitro reperfusion model" Br. J. Pharmacol. 133: 841-848. With regards to the treatment of cancers of the CNS, ibudilast exhibits good. CNS penetration. (Sanftner et al Xenobiotica 2009 39: 964-977).

Ibudilast is also an allosteric inhibitor of p-hydroxyphenylpyruvate (HPP) tautomerase activity of macrophage inhibitory factor (MW) (Cho et al., PNAS-USA, 2010 June 107: 11313-8), thereby inhibiting the catalytic and chemotactic functions of MIF. It was unexpectedly found by the inventors that ibudilast also lowers plasma level of MIF. Such a decrease in MIF plasma level is unexpected since there is no known connection between allosteric inhibition of MIF and WE concentration in plasma. However, since MIF is involved in intracellular signaling through activation of CD74 in a complex with CD44 or the chemokine receptors CXCR2 and CXCR4, both the MIF inhibition and decrease in MIF plasma level by ibudilast can minimize the proinflammatory action of MIF.

As stated previously, a reference to any one or more of the herein-described drugs, in particular ibudilast, is meant to encompass, where applicable, any and all enantiomers, mixtures of enantiomers including racemic mixtures, prodrugs, pharmaceutically acceptable salt forms, hydrates (e.g., monohydrates, dihydrates, etc.), solvates, different physical forms (e.g., crystalline solids, amorphous solids), metabolites, and the like.

Methods of Treatment and Administration

As set forth above, in one aspect, the present disclosure is directed to a methods of preventing metastasis of a cancer in a patient in need thereof, the method comprising, consisting essentially of, or consisting of administering to the patient a therapeutically effective amount of ibudilast, or a pharmaceutical salt thereof.

In another aspect, provided herein are methods of ameliorating metastasis of a cancer in a patient in need thereof, the method comprising, consisting essentially of, or consisting of administering to the patient a therapeutically effective amount of ibudilast, or a pharmaceutical salt thereof.

In another aspect, provided herein are methods of minimizing metastasis of a cancer in a patient in need thereof, the method comprising, consisting essentially of, or consisting of administering to the patient a therapeutically effective amount of ibudilast, or a pharmaceutical salt thereof.

In some embodiments, ibudilast is administered in combination with one or more additional active agents. The one or more additional active agents may be selected from the group consisting of chemotherapy, immunotherapy, epigenetic therapy, or liver-directed therapy. Non-limiting examples of chemotherapy include a combination of dacarbazine and interferon-α; a combination of cisplatin, tamoxifen, and sunitinib; and fotemustine. Non-limiting examples of immunotherapy include immune checkpoint inhibitors such as anti-CTLA-4 therapy, anti-PD-L1 therapy, or anti-PD-1 therapy; tumor infiltrating lymphocytes (TILs); antibody-drug conjugates such as glembatumumab vedotin; and T-cell redirection therapy such as IMCgp100. Immunotherapy includes, but is not limited to, ipilimumab; tremelimumab; nivolumab; pembrolizumab; a combination of ipilimumab and nivolumab; and dendritic cell vaccine. Non-limiting examples of epigenetic therapy include hi stone deacetylase (HDAC) inhibitors, such as vorinostat or PEMDAC (pembrolizumab and entinostat), and bromodomain and extra-terminal (BET) inhibitors, such as PLX51107, Non-limiting examples of liver-directed therapy include isolated hepatic perfusion (IHP) and percutaneous hepatic perfusion (PHP).

In some embodiments, the one or more additional active agents are selected from the group consisting of ICON-1; AU-011; dacarbazine; interferon-α; temozolomide; cisplatin; tamoxifen; treosulfan; fotemustine; crizotinib; ipilimumab; tremelimumab; nivolumab; pembrolizumab; atezolizumab; IMCgp100; glembatumumab; selumetinib; trametinib; sotrastaurin; LXS196; AEB071; BYL719; binimetinib; sunitinib; cabozantinib; sorafenib; carboplatin; paclitaxel; valproic acid; vorinostat; PLX51107; tumor infiltrating lymphocytes; glembatumumab vedontin; and entinostat.

In some embodiments, ibudilast is administered in combination with one or more selected from the group consisting of surgery, brachytherapy, charged-particle radiotherapy, laser therapy, photodynamic therapy, radiofrequency ablation, stereotactic radiotherapy, hepatic intra-arterial infusion, isolated hepatic perfusion, percutaneous hepatic perfusion, and prophylactic liver radiotherapy.

In some embodiments, ibudilast is administered to the patient as adjuvant therapy.

In some embodiments, the cancer is:
a. a cancer of the circulatory system selected from angiosarcoma, fibrosarcoma, rhabdomyosarcoma, liposarcoma, myxoma, rhabdomyoma, fibroma, lipoma and teratoma, cancer of the mediastinum and pleura, or a vascular tumor;
b. a cancer of the respiratory tract selected from cancer of the nasal cavity and middle ear, cancer of accessory sinuses, cancer of larynx, cancer of the trachea, cancer of the bronchus and lung, small cell lung cancer (SCLC), non-small cell lung cancer (NSCLC), bronchogenic carcinoma, squamous cell carcinoma, undifferentiated small cell carcinoma, undifferentiated large cell carcinoma, adenocarcinoma, alveolar (bronchiolar) carcinoma, bronchial adenoma, sarcoma, lymphoma, chondromatous hamartoma, or mesothelioma;

c. a cancer of the gastrointestinal system selected from squamous cell carcinoma, adenocarcinoma, leiomyosarcoma, lymphoma, carcinoma, leiomyosarcoma, ductal adenocarcinoma, insulinoma, glucagonoma, gastrinoma, carcinoid tumors, vipoma, adenocarcinoma, carcinoid tumors, Karposi's sarcoma, leiomyoma, hemangioma, lipoma, neurofibroma, fibroma, adenocarcinoma, tubular adenoma, villous adenoma, hamartoma, or leiomyoma;

d. a cancer of the genitourinary tract selected from adenocarcinoma, Wilm's tumor (nephroblastoma), lymphoma, leukemia, squamous cell carcinoma, transitional cell carcinoma, adenocarcinoma, adenocarcinoma, sarcoma of the prostate, seminoma, teratoma, embryonal carcinoma, teratocarcinoma, choriocarcinoma, interstitial cell carcinoma, fibroma, fibroadenoma, adenomatoid tumors, or lipoma;

e. a cancer of the liver selected from hepatoma (hepatocellular carcinoma), cholangiocarcinoma, hepatoblastoma, angiosarcoma, hepatocellular adenoma, hemangioma, pheochromocytoma, insulinoma, vasoactive intestinal peptide tumor, islet cell tumor, or glucagonoma;

f. a cancer of the bone selected from osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, or giant cell tumors;

g. a cancer of the nervous system selected from primary CNS lymphoma, osteoma, hemangioma, granuloma, xanthoma, osteitis deformans, meningioma, meningiosarcoma, gliomatosis, astrocytoma, medulloblastoma, glioma, ependymoma, germinoma (pinealoma), oligodendroglioma, schwannoma, retinoblastoma, congenital tumors, spinal cord neurofibroma, meningioma, glioma, or sarcoma;

h. a cancer of the reproductive system selected from endometrial carcinoma, cervical carcinoma, pre-tumor cervical dysplasia, ovarian carcinoma, serous cystadenocarcinoma, mucinous cystadenocarcinoma, unclassified carcinoma, granulosa-thecal cell tumors, Sertoli-Leydig cell tumors, dysgerminoma, malignant teratoma, squamous cell carcinoma of the vulva, intraepithelial carcinoma of the vulva, adenocarcinoma of the vulva, fibrosarcoma of the vulva, melanoma of the vulva, vaginal clear cell carcinoma, vaginal squamous cell carcinoma, vaginal botryoid sarcoma (embryonal rhabdomyosarcoma), carcinoma of the fallopian tubes placental cancer, penile cancer, prostate cancer, or testicular cancer;

i. cancer of the hematologic system selected from myeloid, acute lymphoblastic leukemia, chronic lymphocytic leukemia, myeloproliferative diseases, multiple myeloma, myelodysplastic syndrome, Hodgkin's disease, or non-Hodgkin's lymphoma;

j. a cancer of the oral cavity selected from lip cancer, tongue cancer, gum cancer, floor of mouth cancer, palate cancer, parotid gland cancer, salivary gland cancer, tonsil cancer, cancer of the oropharynx, cancer of the nasopharynx, pyriform sinus cancer, or cancer of the hypopharynx;

k. a cancer of the skin selected from malignant melanoma, cutaneous melanoma, basal cell carcinoma, squamous cell carcinoma, Karposi's sarcoma, moles dysplastic nevi, lipoma, angioma, dermatofibroma, or keloidal cancer; or l. a cancer selected from cancer of the adrenal glands, neuroblastoma, cancer of connective and soft tissue, cancer of the retroperitoneum and peritoneum, eye cancer, intraocular melanoma, cancer of adnexa, breast cancer, head or/and neck cancer, anal cancer, thyroid cancer, parathyroid cancer, cancer of the adrenal gland, cancer of the endocrine glands and related structures, secondary and unspecified malignant neoplasm of lymph nodes, secondary malignant neoplasm of respiratory and digestive systems, or secondary malignant neoplasm of other sites.

In some embodiments, the cancer is breast cancer, prostate cancer, liver cancer, colon cancer, cervical cancer, uterine cancer, ovarian cancer, lung cancer, head and/or neck cancer, pancreatic cancer, gastric cancer, or renal cancer. In some embodiments, the cancer is one or more solid tumors.

In some embodiments, the cancer is eye cancer. In some embodiments, the eye cancer is uveal melanoma.

In some embodiments, ibudilast or a pharmaceutically acceptable salt thereof is administered at a daily dosage amount ranging from about 0.1 mg to 720 mg daily, from about 30 mg to 200 mg daily, from about 40 mg to 600 mg daily, or from about 100 mg to 480 mg daily.

Ibudilast administration may be accomplished through various modes of delivery of ibudilast comprising formulations. Preferred methods of delivery of ibudilast-based therapeutic formulations include systemic and localized delivery. Such routes of administration include but are not limited to, oral, intra-arterial, intrathecal, intraspinal, intramuscular, intraperitoneal, intranasal, and inhalation routes.

More particularly, an ibudilast-based formulation of the present disclosure may be administered for therapy by any suitable route, including without limitation, oral, rectal, nasal, topical (including transdermal, aerosol, buccal and sublingual), vaginal, parenteral (including subcutaneous, intravenous, intramuscular, and intradermal), intrathecal, and pulmonary. In some embodiments, the ibudilast-based formulation is administered orally. In some embodiments, the ibudilast-based formulation is administered through an injection. The preferred route will, of course, vary with the condition and age of the recipient, the particular syndrome being treated, and the specific combination of drugs employed.

In some embodiments, the ibudilast or pharmaceutically acceptable salt thereof is administered orally. In some embodiments, the ibudilast or pharmaceutically acceptable salt thereof is administered through an injection.

An ibudilast composition of the present disclosure, when comprising more than one active agent, may be administered as a single combination composition comprising a combination of ibudilast and at least one additional active agent. In terms of patient compliance and ease of administration, such an approach is preferred, since patients are often averse to taking multiple pills or dosage forms, often multiple times daily, over the duration of treatment. Alternatively, the combination of the disclosure is administered as separate dosage forms. In instances in which the drugs comprising the therapeutic composition of the disclosure are administered as separate dosage forms and co-administration is required, ibudilast and each of the additional active agents may be administered simultaneously, sequentially in any order, or separately.

Dosages

Therapeutic amounts can be empirically determined and will vary with the particular condition being treated, the subject, and the efficacy and toxicity of each of the active agents contained in the composition. The actual dose to be administered will vary depending upon the age, weight, and general condition of the subject as well as the severity of the condition being treated, the judgment of the health care professional, and particular combination being administered.

Therapeutically effective amounts can be determined by those skilled in the art, and will be adjusted to the requirements of each particular case. Generally, a therapeutically effective amount of ibudilast or pharmaceutically acceptable salt thereof will range from a total daily dosage of about 0.1 mg/day to 720 mg/day, about 40-600 mg/day, or about 100-480 mg/day, or more preferably, in an amount between about 1-240 mg/day, about 30-240 mg/day, about 30-200 mg/day, about 30-120 mg/day, about 1-120 mg/day, about 50-150 mg/day, about 60-150 mg/day, about 60-120 mg/day, or about 60-100 mg/day, administered as either a single dosage or as multiple dosages. In some embodiments, the therapeutically effective amount of ibudilast or pharmaceutically acceptable salt thereof is from about 30-200 mg/day, administered as either a single dosage or as multiple dosages. In some embodiments, the therapeutically effective amount of ibudilast or pharmaceutically acceptable salt thereof is from about 60-600 mg/day, administered as either a single dosage or as multiple dosages. In some embodiments, the therapeutically effective amount of ibudilast or pharmaceutically acceptable salt thereof is from about 100-480 mg/day, administered as either a single dosage or as multiple dosages. In some embodiments, multiple dosages include two, three, or four doses per day.

Preferred dosage amounts include dosages greater than about 20 mg BID or TID. That is to say, a preferred dosage amount is greater than about 30 mg/day, 60 mg/day, 90 mg/day, 100 mg/clay, 120 mg/day, 150 mg/day, 180 mg/day, 210 mg/day, 240 mg/clay, 270 mg/day, 300 mg/day, 360 mg/day, 400 mg/day, 440 mg/day, 480 mg/day, 520 mg/day, 580 mg/day, 600 mg/day, 620 mg/day, 640 mg/day, 680 mg/day, and 720 mg/day or more.

In some embodiments, the therapeutically effective amount of ibudilast or pharmaceutically acceptable salt thereof is at least 30 mg/day, at least 40 mg/day, at least 50 mg/day, at least 60 mg/day, at least 70 mg/day, at least 80 mg/day, at least 90 mg/day, at least 100 mg/day, at least 110 mg/day, at least 120 mg/day, at least 130 mg/day, at least 140 mg/day, at least 150 mg/day, at least 160 mg/day, at least 170 mg/day, at least 180 mg/day, at least 190 mg/day, at least 200 mg/day, at least 225 mg/day, at least 250 mg/day, at least 275 mg/day, at least 300 mg/day, at least 325 mg/day, at least 350 mg/day, at least 375 mg/day, at least 400 mg/day, at least 425 mg/day, at least 450 mg/day, at least 475 mg/day, at least 500 mg/day, at least 525 mg/day, at least 550 mg/day, at least 575 mg/day, at least 600 mg/day, at least 625 mg/day, at least 650 mg/day, at least 675 mg/day, at least 700 mg/day, or at least 720 mg/day. In some embodiments, the therapeutically effective amount of ibudilast or pharmaceutically acceptable salt thereof is at least 60 mg/day. In some embodiments, the therapeutically effective amount of ibudilast or pharmaceutically acceptable salt thereof is at least 100 mg/day.

Depending upon the dosage amount and precise condition to be treated, administration can be one, two, three, or four times daily for a time course of one day to several days, weeks, months, and even years, and may even be for the life of the patient. Illustrative dosing regimens will last a period of at least about a week, from about 1-4 weeks, from 1-3 months, from 1-6 months, from 1-52 weeks, from 1-24 months, or longer. In some embodiments, the ibudilast or the pharmaceutically acceptable salt thereof is administered for 1, 2, 3, 4, 5, 7, 8, 10, 11, 12, 13, 14, 15, 16, 17, 18, 19, 20, 21, 22, 23, 24, 25, 26, 27, 28, 29, or 30 days. In some embodiments, the ibudilast or the pharmaceutically acceptable salt thereof is administered for three months or less. In some embodiments, the ibudilast or the pharmaceutically acceptable salt thereof is administered for at least three months. In some embodiments, the ibudilast or the pharmaceutically acceptable salt thereof is administered for at least six months. In some embodiments, the ibudilast or the pharmaceutically acceptable salt thereof is administered for 1, 2, 3, 4, 5, 6, 7, 8, 9, 10, 11, or 12 months, or more. In some embodiments, the ibudilast or the pharmaceutically acceptable salt thereof is administered for about 1, 2, 3, 4, 5, 6, 7, 8, 9, or 10 years, or more. In some embodiments, the ibudilast or the pharmaceutically acceptable salt thereof is administered for at least 1 year. In some embodiments, the ibudilast or the pharmaceutically acceptable salt thereof is administered for at least 2 years. In some embodiments, the ibudilast or the pharmaceutically acceptable salt thereof is administered as a one-time single dose.

In some embodiments, the therapeutically effective amount of ibudilast or the pharmaceutically acceptable salt thereof is administered in a single dosage per day. In some embodiments, the therapeutically effective amount of ibudilast or the pharmaceutically acceptable salt thereof is administered in two dosages per day. In some embodiments, the therapeutically effective amount of ibudilast or the pharmaceutically acceptable salt thereof is administered in three dosages per day. In some embodiments, the therapeutically effective amount of ibudilast or the pharmaceutically acceptable salt thereof is administered in four dosages per day. In some embodiments, the therapeutically effective amount of ibudilast or the pharmaceutically acceptable salt thereof is administered continually.

In some embodiments, the ibudilast or pharmaceutically acceptable salt thereof is administered at least once daily. In some embodiments, the ibudilast, or pharmaceutically acceptable salt thereof is administered at least twice daily. In some embodiments, the ibudilast or pharmaceutically acceptable salt thereof is administered once daily. In some embodiments, the ibudilast or pharmaceutically acceptable salt thereof is administered twice daily.

Practically speaking, a unit dose of any given composition of the disclosure or active agent can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth.

Formulations

Ibudilast may be administered in a composition of formulation which may optionally contain one or more additional components as described below.

Excipients/Carriers

In addition to ibudilast or a pharmaceutically acceptable salt thereof, the compositions of the disclosure may further comprise one or more pharmaceutically acceptable excipients or carriers. Exemplary excipients include, without limitation, polyethylene glycol (PEG), PEG 400, (2-Hydroxypropyl)-β-cyclodextrin, hydrogenated castor oil (FICO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

A composition of the disclosure may include one or more carbohydrates such as a sugar, a derivatized sugar such as an alditol, aldonic acid, an esterified sugar, and/or a sugar polymer. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Also suitable for use in the compositions of the disclosure are potato and corn-based starches such as sodium starch glycolate and directly compressible modified starch.

Further representative excipients include inorganic salt or buffers such as citric acid, sodium chloride, potassium chloride, sodium sulfate, potassium nitrate, sodium phosphate monobasic, sodium phosphate dibasic, and combinations thereof.

A composition of the disclosure may also contain one or more antioxidants. Antioxidants are used to prevent oxidation, thereby preventing the deterioration of the drug(s) or other components of the preparation. Suitable antioxidants for use in the present disclosure include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional exemplary excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations. In some embodiments, the surfactant may comprise polyethoxylated castor oil derivatives (e.g., Cremophor E L, Kolliphor E L P, and the like). Other non-limiting excipients include alcohol (e.g., ethanol), propylene glycol, glyderol, or polyethyleneglycol (PEG).

Further, a composition of the disclosure may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Non-limiting examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumarase, and combinations thereof.

The amount of any individual excipient in the composition will vary depending on the role of the excipient, the dosage requirements of the active agent components, and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15% to about 95% by weight of the excipient. In general, the amount of excipient present in an ibudilast composition of the disclosure is selected from the following: at least about 7%, 5%, 10%, 15%, 70%, 25%, 30%, 35%, 40%, 45%, 50%, 55%, 60%, 65%, 70%, 75%, 80%, 85%, 90%, or even 95% by weight.

These foregoing pharmaceutical excipients along with other excipients are described in "Remington: The Science & Practice of Pharmacy," 19th ed., Williams & Williams, (1995), the "Physician's Desk Reference", 52.sup.nd ed., Medical Economics, Montvale, N.J. (1998), and Kibbe, A. H., Handbook of Pharmaceutical Excipients, 3.sup.rd Edition, American Pharmaceutical Association, Washington, D.C., 2000.

Sustained Delivery Formulations

Preferably, the compositions are formulated in order to improve stability and extend the half-life of ibudilast or the pharmaceutically acceptable salt thereof. For example, ibudilast or the pharmaceutically acceptable salt thereof may be delivered in a controlled or extended-release formulation. Controlled or extended-release formulations are prepared by incorporating ibudilast or the pharmaceutically acceptable salt thereof into a carrier or vehicle such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. Additionally, ibudilast or the pharmaceutically acceptable salt thereof can be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery et al., Pharm. Res. (1993) 10:362-368; and McGee et al., J. Microencap. (1996).

Extended release polymers suitable for this purpose are known in the art and include hydrophobic polymers such as cellulose ethers. Non-limiting examples of suitable cellulose ethers include ethyl cellulose, cellulose acetate and the like; polyvinyl esters such as polyvinyl acetate, polyacrylic acid esters, methacrylic and acrylate polymers (pH-independent types); high molecular weight polyvinyl alcohols and waxes such as fatty acids and glycerides, methacrylic acid ester neutral polymers, polyvinyl alcohol-maleic anhydride copolymers and the like; ethylacrylate-methylmethacrylate copolymers; aminoalkyl methacrylate copolymers; and mixtures thereof.

Delivery Forms

The ibudilast or pharmaceutically acceptable salt thereof compositions described herein encompass all types of formulations, and in particular, those that are suited for systemic or intrathecal administration. Oral dosage forms include tablets, lozenges, capsules, syrups, oral suspensions, emulsions, granules, and pellets. In some embodiments, the oral dosage form is a tablet. In some embodiments, the tablet is an extended release tablet. In some embodiments, the oral dosage form is a capsule. In some embodiments, the capsule is an extended release capsule.

Alternative formulations include aerosols, transdermal patches, gels, creams, ointments, suppositories, powders or lyophilates that can be reconstituted, as well as liquids. Examples of suitable diluents for reconstituting solid compositions, e.g., prior to injection, include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned. Preferably, an ibudilast or pharmaceutically acceptable salt thereof composition of the disclosure is one suited for oral administration.

In turning now to oral delivery formulations, tablets can be made by compression or molding, optionally with one or more accessory ingredients or additives. Compressed tablets are prepared, for example, by compressing in a suitable tabletting, machine, the active ingredients in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) and/or surface-active or dispersing agent.

Molded tablets are made, for example, by molding in a suitable tableting machine, a mixture of powdered compounds moistened with an inert liquid diluent. The tablets may optionally be coated or scored, and may be formulated so as to provide slow or controlled release of the active ingredients, using, for example, hydroxypropylmethyl cellulose in varying proportions to provide the desired release profile. Tablets may optionally be provided with a coating, such as a thin film, sugar coating, or an enteric coating to provide release in parts of the gut other than the stomach. Processes, equipment, and toll manufacturers for tablet and capsule making are well-known in the art.

Formulations for topical administration in the mouth include lozenges comprising the active ingredients, generally in a flavored base such as sucrose and acacia or tragacanth and pastilles comprising the active ingredients in an inert base such as gelatin and glycerin or sucrose and acacia.

A pharmaceutical composition for topical administration may also be formulated as an ointment, cream, suspension, lotion, powder, solution, paste, gel, spray, aerosol or oil.

Alternatively, the formulation may be in the form of a patch (e.g., a transdermal patch) or a dressing such as a bandage or adhesive plaster impregnated with active ingredients and optionally one or more excipients or diluents. Topical formulations may additionally include a compound that enhances absorption or penetration of the ingredients through the skin or other affected areas, such as dimethylsulfoxidem bisabolol, oleic acid, isopropyl myristate, and limonene, to name a few.

For emulsions, the oily phase is constituted from known ingredients in a known manner. While this phase may comprise merely an emulsifier (otherwise known as an emulgent), it desirably comprises a mixture of at least one emulsifier with a fat and/or an oil. Preferably, a hydrophilic emulsifier is included together with a lipophilic emulsifier that acts as a stabilizer. Together, the emulsifier(s) with or without stabilizer(s) make up the so-called emulsifying wax, and the wax together with the oil and/or fat make up the so-called emulsifying ointment base which forms the oily dispersed phase of cream formulations. Illustrative emulgents and emulsion stabilizers include Tween 60, Span 80, cetostearyl alcohol, myristyl alcohol, glyceryl monostearate and sodium lauryl sulfate.

Formulations for rectal administration are typically in the form of a suppository with a suitable base comprising, for example, cocoa butter or a salicylate.

Formulations suitable for vaginal administration generally take the form of a suppository, tampon, cream, gel, paste, foam or spray.

Formulations suitable for nasal administration, wherein the carrier is a solid, include a coarse powder having a particle size, for example, in the range of about 20 to about 500 microns. Such a formulation is typically administered by rapid inhalation through the nasal passage, e.g., from a container of the powder held in proximity to the nose. Alternatively, a formulation for nasal delivery may be in the form of a liquid, e.g., a nasal spray or nasal drops.

Aerosolizable formulations for inhalation may be in dry powder form (e.g., suitable for administration by a dry powder inhaler), or, alternatively, may be in liquid form, e.g., for use in a nebulizer. Nebulizers for delivering an aerosolized solution include the AERx® (Aradigm), the Ultravent® (Mallinckrodt), and the Acorn II® (Marquest Medical Products). A composition of the disclosure may also be delivered using a pressurized, metered dose inhaler (MDI), e.g., the Ventolin® metered dose inhaler, containing a solution or suspension of a combination of drugs as described herein in a pharmaceutically inert liquid propellant, e.g., a chlorofluorocarbon or fluorocarbon.

Formulations suitable for parenteral administration include aqueous and non-aqueous isotonic sterile solutions suitable for injection, as well as aqueous and non-aqueous sterile suspensions.

Parenteral formulations of the disclosure are optionally contained in unit-dose or multi-dose sealed containers, for example, ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the types previously described.

A formulation of the disclosure may also be an extended release formulation, such that each of the drug components is released or absorbed slowly over time, when compared to a non-sustained release formulation. Sustained release formulations may employ pro-drug forms of the active agent, delayed-release drug delivery systems such as liposomes or polymer matrices, hydrogels, or covalent attachment of a polymer such as polyethylene glycol to the active agent.

In addition to the ingredients particularly mentioned above, the formulations of the disclosure may optionally include other agents conventional in the pharmaceutical arts and particular type of formulation being employed, for example, for oral administration forms, the composition for oral administration may also include additional agents as sweeteners, thickeners or flavoring agents.

Kits

Also provided herein is a kit containing at least one composition of the disclosure, accompanied by instructions for use.

in some embodiments, the kit contains at least one combination composition described herein, accompanied by instructions for use. For example, in instances in which each of the drugs themselves are administered as individual or separate dosage forms, the kit comprises ibudilast in addition to each of the drugs making up the composition of the disclosure, along with instructions for use. The drug components may be packaged in any manner suitable for administration, so long as the packaging, when considered along with the instructions for administration, clearly indicates the manner in which each of the drug components is to be administered.

For example, for an illustrative kit comprising ibudilast and one other active agent, the kit may be organized by any appropriate time period, such as by day. As an example, for Day 1, a representative kit may comprise unit dosages of each of ibudilast and the one other active agent. If each of the drugs is to be administered twice daily, then the kit may contain, corresponding to Day 1, two rows of unit dosage forms of each of ibudilast and the one other active agent, along with instructions for the timing of administration. Alternatively, if one or more of the drugs differs in the timing or quantity of unit dosage form to be administered in comparison to the other drug members of the combination, then such would be reflected in the packaging and instructions. Various embodiments according to the above may be readily envisioned, and would of course depend upon the particular combination of drugs, in addition to ibudilast, employed for treatment, their corresponding dosage forms, recommended dosages, intended patient population, and the like. The packaging may be in any form commonly employed for the packaging of pharmaceuticals, and may utilize any of a number of features such as different colors, wrapping, tamper-resistant packaging, blister packs, desiccants, and the like.

It is to be understood that while the disclosure has been described in conjunction with preferred specific embodiments, the foregoing description as well as the examples that follow are intended to illustrate and not limit the scope of the disclosure. Other aspects, advantages and modifications within the scope of the disclosure will be apparent to those skilled in the art to which the disclosure pertains.

All references mentioned in this application, including any patents, published patent applications, books, handbooks, journal publications, or the FDA Orange Book are hereby incorporated by reference herein, in their entirety.

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends and advantages inherent herein. The present examples, along with the methods described herein are presently representative of embodiments and are exemplary, and are not intended as limitations on the scope of the disclosure. Changes therein and other uses which are encompassed within the spirit of the disclosure as defined by the scope of the claims will occur to those skilled in the art.

EXAMPLES

Example 1

Ibudilast in In Vitro Uveal Melanoma (UM) Assays

Exosome isolation. Exosomes were isolated from UM cell lines kept in serum-free media for 24 hrs. The media was collected and subjected to serial centrifugation steps starting with a spin at 3,000×g to remove dead cells and cell debris. The supernatant from this step is spun at 20,000×g to pellet microvesicles and large EVs. Lastly, the supernatant from this step is centrifuged at 100,000×g to pellet the exosome fraction.

Transwell migration assay. The in vitro migration assays were performed with 5×104 Omm1.3 cells seeded in 500 µL serum-free medium on BioCoat Matrigel Invasion Chambers (BD Biosciences). The conditioned media of the hepatocytes treated or untreated with UM-exosome was used as chemoattractant in the lower chamber. The cells were also treated with vehicle (DMSO), 0.25 µM crizotinib or 25 µM ibudilast for 24 hrs. The migrated cells were fixed in 100% methanol and stained with 1% Toluidine Blue. Images of stained cells were taken through a microscope and quantified by counting cells in triplicate samples.

Wound healing assay. Omm1.3 and MP41 cells were scratched with a sterile 200 µL pipette tip. Cells were washed in PBS and replaced with fresh RPMI 1640 complete media, or hepatocyte conditioned media (HCM) pretreated with UM-exo. Images of the wounded area were recorded using an inverted phase-contrast microscope at the indicated time points.

Figure 1B:
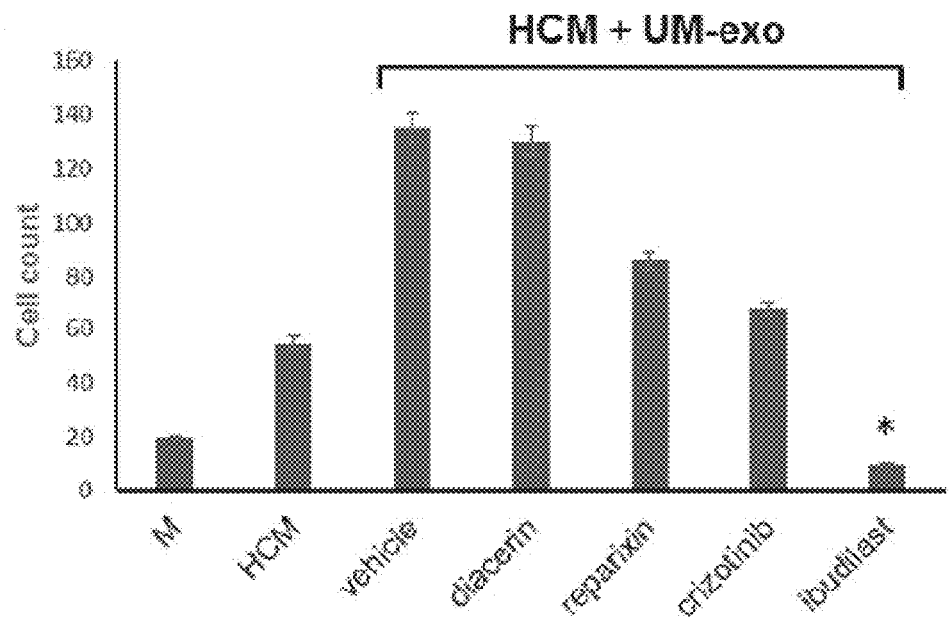
FIG. 1B depicts migrated cell count under the microscope from the trans-well migration assay, three fields for each condition. Experiments were repeated three times ±sd, p<0.001.
Figure 1C:
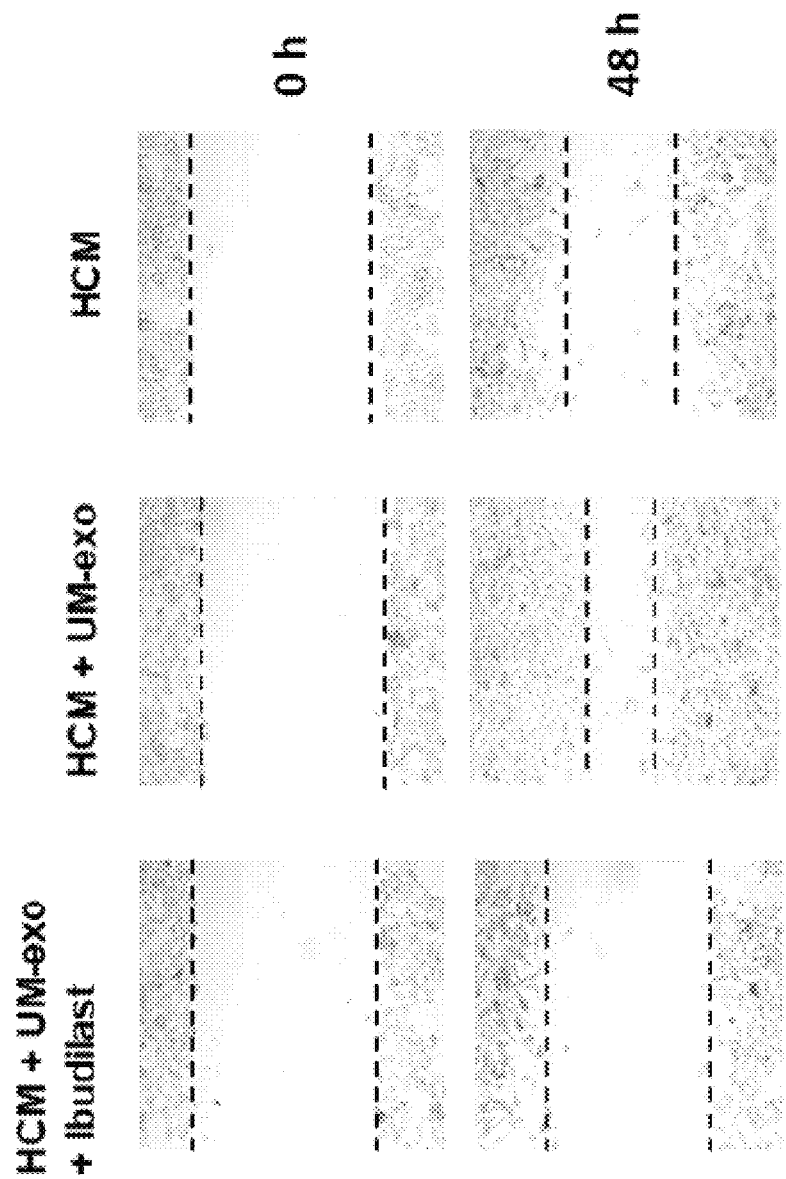
FIG. 1C depicts Omm1.3 cells in scratch assays, in which after the scratch, the cells were incubated with control HCM or with HCM of hepatocytes exposed to UM-exosomes with or without 25 µM ibudilast. Pictures were taken at zero time-point or after 48 hours under a microscope at 10× magnification.

Diacerein, reparixin, crizotinib and ibudilast were evaluated in the migration assay. As shown in FIG. 1A, most inhibitors had little or partial effects in blocking UM cell migration toward UM-exosome-stimulated hepatocyte conditioned media (HCM). In contrast, ibudilast dramatically inhibited cell migration. Quantitation of migrated cells is summarized in FIG. 1B, In addition, ibudilast suppressed the wound healing ability of UM cell lines Omm1.3 (FIG. 1C) and MP41 (data not shown), when exposed to HCM and UM-exosome (HCM+UM-exo).

Example 2

Ibudilast in Metastatic Uveal Melanoma (UM) Mouse Model

Mice were injected intravenously with vehicle (PBS) or 10 µg UM-exosome isolated from 92.1 9 cells in 100 µL PBS for 7 days. Subsequently, GFP-Luc-Omm1.3 cells were retro-orbitally injected in the mice as described in Surriga et al. (Mol. Cancer Ther., 2013, 12:2817-26). Ibudilast was dissolved to a concentration of 1 mg/ml in physiological saline containing 10% v/v of polyoxyethylene hydrogenated castor oil 60 (HCO60). A week later, the mice were treated daily with vehicle or 7.5 mg/kg ibudilast i.p. and monitored for the development of metastasis. All mice presented strong signals in the eyes as the site of injection. The mice were monitored weekly for luminescence with luciferin (Gold Biotechnology). After 7 weeks the livers and lungs were collected and analyzed for luminescence. Experiments were carried out under an Institutional Animal Care and Use Committee—approved (IACUC) protocol, and Institutional guidelines for the proper and humane use of animals were followed. Statistical significance was determined by 2-sample Student t-test.

Figure 2A:
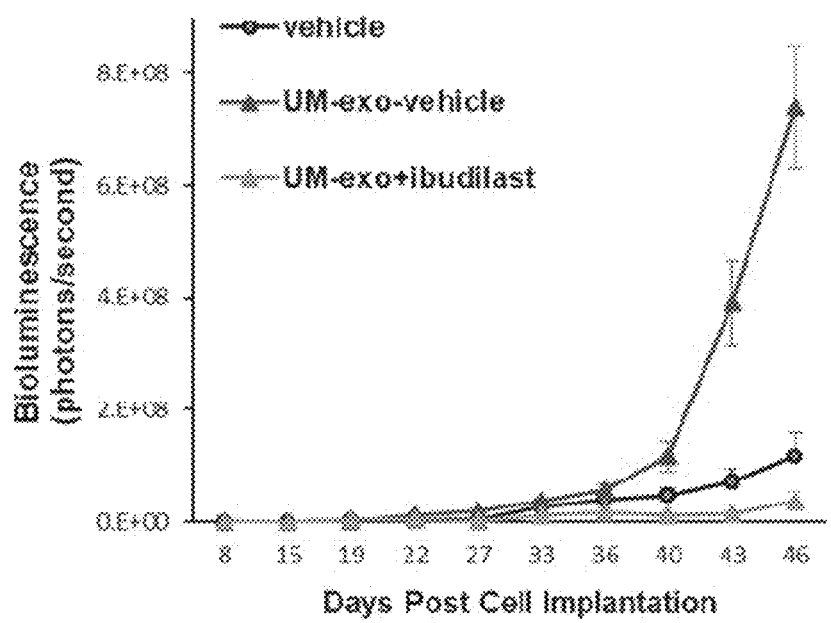
FIG. 2A depicts quantification of bioluminescence intensity for each mouse in the abdominal region, while excluding bioluminescence in the eyes, in an evaluation of ibudilast in a metastatic UM mouse model. The mean was calculated for each cohort, ±SEM, p<0.05 comparing ibudilast treatment versus vehicle.
Figure 2B:
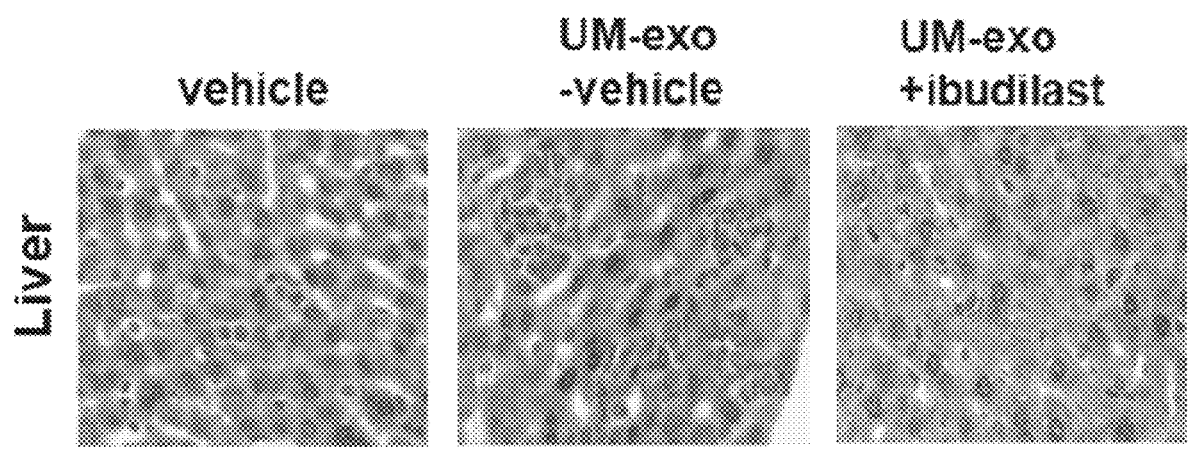
FIG. 2B depicts representative images of H&E-stained mouse liver sections from the metastatic UM mouse model.

By measuring bioluminescence signal intensity exclusively in the abdominal region, it was found that the UM-exosome-treated mice developed metastasis within 5 weeks after cell injection, while signals of metastasis were still modest in vehicle control mice. Furthermore, the exosome-educated group treated with ibudilast showed inhibition of metastatic spread. The quantification of bioluminescence over time for each group is shown in FIG. 2A, Necropsy, images from representative mice show that mice pre-treated with UM-exosome had higher bioluminescence in lungs and livers compared to controls, whereas there was no bioluminescence signal in organs of UM-exosome and ibudilast-treated animals. H&E staining of liver sections from all three cohorts verified the presence of cancer cell clusters in UM-exosome-educated mice treated with vehicle, but not in the livers of UM-exosome-educated mice treated with ibudilast (FIG. 2B).

CERTAIN EMBODIMENTS

Embodiment 1. A method of preventing metastasis of a cancer in a patient in need thereof, the method comprising:
administering to the patient a therapeutically effective amount of ibudilast, or a pharmaceutical salt thereof.

Embodiment 2. A method of ameliorating metastasis of a cancer in a patient in need thereof, the method comprising:
administering to the patient a therapeutically effective amount of ibudilast, or a pharmaceutical salt thereof.

Embodiment 3. A method of minimizing metastasis of a cancer in a patient in need thereof, the method comprising:
administering to the patient a therapeutically effective amount of ibudilast, or a pharmaceutical salt thereof.

Embodiment 4. The method of any one of Embodiments 1-3, wherein ibudilast is administered in combination with one or more additional active agents.

Embodiment 5. The method of Embodiment 4, wherein the one or more additional active agents are selected from the group consisting of chemotherapy, immunotherapy, epigenetic therapy, and liver-directed therapy.

Embodiment 6. The method of Embodiment 4, wherein the one or more additional active agents are selected from the group consisting of ICON-1; AU-011; dacarbazine; interferon-α; temozolomide; cisplatin; tamoxifen; treosulfan; fotemustine; crizotinib; ipilimumab; tremelimuinab; nivolumab; pembrolizumab; atezolizumab; 1MCgp100; glembatumumab; selumetinib; trametinib; sotrastaurin; LXS196; AEB071; BYL719; binimetinib; sunitinib; cabozantinib; sorafenib; carboplatin; paclitaxel; valproic acid; vorinostat; PLX51107; tumor infiltrating lymphocytes; glembatumumab vedontin; and entinostat.

Embodiment 7. The method of any one of Embodiments 1-3, wherein ibudilast is administered in combination with one or more selected from the group consisting of surgery, brachytherapy, charged-particle radiotherapy, laser therapy, photodynamic therapy, radiofrequency ablation, stereotactic radiotherapy, hepatic intra-arterial infusion, isolated hepatic perfusion, percutaneous hepatic perfusion, and prophylactic liver radiotherapy.

Embodiment 8. The method of any one of Embodiments 1-7, wherein ibudilast is administered to the patient as adjuvant therapy.

Embodiment 9. The method of any one of Embodiments 1-8, wherein the cancer is:
a. a cancer of the circulatory system selected from angiosarcoma, fibrosarcoma, rhabdomyosarcoma, liposarcoma, myxoma, rhabdomyoma, fibroma, lipoma and teratoma, cancer of the mediastinum and pleura, or a vascular tumor;
b. a cancer of the respiratory tract selected from cancer of the nasal cavity and middle ear, cancer of accessory sinuses, cancer of larynx, cancer of the trachea, cancer of the bronchus and lung, small cell lung cancer (SCLC), non-small cell lung cancer (NSCLC), bronchogenic carcinoma, squamous cell carcinoma, undifferentiated small cell carcinoma, undifferentiated large cell carcinoma, adenocarcinoma, alveolar (bronchiolar) carcinoma, bronchial adenoma, sarcoma, lymphoma, chondromatous hamartoma, or mesothelioma;
c. a cancer of the gastrointestinal system selected from squamous cell carcinoma, adenocarcinoma, leiomyosarcoma, lymphoma, carcinoma, leiomyosarcoma, ductal adenocarcinoma, insulinoma, glucagonoma, gastrinoma, carcinoid tumors, vipoma, adenocarcinoma, carcinoid tumors, Karposi's sarcoma, leiomyoma, hemangioma, lipoma, neurofibroma, fibroma, adenocarcinoma, tubular adenoma, villous adenoma, hamartoma, or leiomyoma;
d. a cancer of the genitourinary tract selected from adenocarcinoma, Wilm's tumor (nephroblastoma), lymphoma, leukemia, squamous cell carcinoma, transitional cell carcinoma, adenocarcinoma, adenocarcinoma, sarcoma of the prostate, seminoma, teratoma, embryonal carcinoma, teratocarcinoma, choriocarcinoma, interstitial cell carcinoma, fibroma, fibroadenoma, adenomatoid tumors, or lipoma;
e. a cancer of the liver selected from hepatoma (hepatocellular carcinoma), cholangiocarcinoma, hepatoblastoma, angiosarcoma, hepatocellular adenoma, hemangioma, pheochromocytoma, insulinoma, vasoactive intestinal peptide tumor, islet cell tumor, or glucagonoma;
f. a cancer of the bone selected from osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, or giant cell tumors;
g. a cancer of the nervous system selected from primary CNS lymphoma, osteoma, hemangioma, granuloma, xanthoma, osteitis deformans, meningioma, meningiosarcoma, gliomatosis, astrocytoma, medulloblastoma, glioma, ependymoma, germinoma (pinealoma), oligodendroglioma, schwannoma, retinoblastoma, congenital tumors, spinal cord neurofibroma, meningioma, glioma, or sarcoma;
h. a cancer of the reproductive system selected from endometrial carcinoma, cervical carcinoma, pre-tumor cervical dysplasia, ovarian carcinoma serous cystadenocarcinoma, mucinous cystadenocarcinoma, unclassified carcinoma, granulosa-thecal cell tumors, Sertoli-Leydig cell tumors, dysgerminoma, malignant teratoma, squamous cell carcinoma of the vulva, intraepithelial carcinoma of the vulva, adenocarcinoma of the vulva, fibrosarcoma of the vulva, melanoma of the vulva, vaginal clear cell carcinoma, vaginal squamous cell carcinoma, vaginal botryoid sarcoma (embryonal rhabdomyosarcoma), carcinoma of the fallopian tubes placental cancer, penile cancer, prostate cancer, or testicular cancer;
i. cancer of the hematologic system selected from myeloid, acute lymphoblastic leukemia, chronic lymphocytic leukemia, myeloproliferative diseases, multiple myeloma, myelodysplastic syndrome, Hodgkin's disease, or non-Hodgkin's lymphoma;
j. a cancer of the oral cavity selected from lip cancer, tongue cancer, gum cancer, floor of mouth cancer, palate cancer, parotid gland cancer, salivary gland cancer, tonsil cancer, cancer of the oropharynx, cancer of the nasopharynx, pyriform sinus cancer, or cancer of the hypopharynx;
k. a cancer of the skin selected from malignant melanoma, cutaneous melanoma, basal cell carcinoma, squamous cell carcinoma, Karposi's sarcoma, moles dysplastic nevi, lipoma, angioma, dermatofibroma, or keloidal cancer; or l. a cancer selected from cancer of the adrenal glands, neuroblastoma, cancer of connective and soft tissue, cancer of the retroperitoneum and peritoneum, eye cancer, intraocular melanoma, cancer of adnexa, breast cancer, head or/and neck cancer, anal cancer, thyroid cancer, parathyroid cancer, cancer of the adrenal gland, cancer of the endocrine glands and related structures, secondary and unspecified malignant neoplasm of lymph nodes, secondary malignant neoplasm of respiratory and digestive systems, or secondary malignant neoplasm of other sites.

Embodiment 10. The method of any one of Embodiments 1-9, wherein the cancer is eye cancer.

Embodiment 11. The method of Embodiment 10, wherein the eye cancer is uveal melanoma.

Embodiment 12. The method of any one of Embodiments 1-11, wherein ibudilast, or the pharmaceutically acceptable salt thereof, is administered for at least 3 months.

Embodiment 13. The method of any one of Embodiments 1-11, wherein ibudilast, or the pharmaceutically acceptable salt thereof, is administered for at least six months.

Embodiment 14. The method of any one of Embodiments 1-11, wherein ibudilast, or the pharmaceutically acceptable salt thereof, is administered for at least one year.

Embodiment 15. The method of any one of Embodiments 1-11, wherein ibudilast, or the pharmaceutically acceptable salt thereof, is administered for at least two years.

Embodiment 16. The method of any one of Embodiments 1-15, wherein ibudilast, or the pharmaceutically acceptable salt thereof, is administered at least once daily.

Embodiment 17. The method of any one of Embodiments 1-16, wherein ibudilast, or the pharmaceutically acceptable salt thereof, is administered orally.

Embodiment 18. The method of any one of Embodiments 1-17, wherein the therapeutically effective amount of ibudilast, or the pharmaceutically acceptable salt thereof, is from 0.1 mg to 720 mg per day.

Embodiment 19. The method of any one of Embodiments 1-17, wherein the therapeutically effective amount of ibudilast, or the pharmaceutically acceptable salt thereof, is at least 30 mg/day.

Embodiment 20. The method of any one of Embodiments 1-17, wherein the therapeutically effective amount of ibudilast, or the pharmaceutically acceptable salt thereof, is from 30 mg to 200 mg per day.

Embodiment 21. The method of any one of Embodiments 1-17, wherein the therapeutically effective amount of ibudilast, or the pharmaceutically acceptable salt thereof is 60 mg to 600 mg daily.

Embodiment 22. The method of any one of Embodiments 1-17, wherein the therapeutically effective amount of ibudilast, or the pharmaceutically acceptable salt thereof, is 100 mg to 480 mg daily.

Embodiment 23. The method of any one of Embodiments 1-17, wherein the therapeutically effective amount of ibudilast, or the pharmaceutically acceptable salt thereof, is selected from the group consisting of 30 mg/day, 60 mg/day, 90 mg/day, 100 mg/day, 120 mg/day, 150 mg/day, 180 mg/day, 210 mg/day, 240 mg/day, 270 mg/day, 300 mg/day, 360 mg/day, 400 mg/day, 440 mg/day, 480 mg/day, 52.0 mg/day, 580 mg/day, 600 mg/day, 620 trig/day, 640 mg/day, 680 mg/day, and 720 mg/day.

Embodiment 24. The method of any one of Embodiments 1-23, wherein the therapeutically effective amount is administered as a single dose or is divided into two, three, or four doses.

Embodiment 25. The method of any one of Embodiments 1-24, wherein ibudilast is administered continually.

EQUIVALENTS

It should be understood that although the present disclosure has been specifically disclosed by certain embodiments and optional features, modification, improvement and variation of the disclosures embodied disclosed herein may be resorted to by those skilled in the art, and that such modifications, improvements and variations are considered to be within the scope of this disclosure. The materials, methods, and examples provided here are representative of certain embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

The use of the term "or" in the claims is used to mean "and/or" unless explicitly indicated to refer to alternatives only or the alternatives are mutually exclusive, although the disclosure supports a definition that refers to only alternatives and "and/or."

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above, Finally, as will be understood by one skilled in the art, a range includes each individual member.

Other embodiments are set forth in the following claims.

What is claimed is:

1. A method of preventing, ameliorating, or minimizing metastasis of eye cancer in a patient in need thereof, the method comprising:
    administering to the patient a therapeutically effective amount of ibudilast, or a pharmaceutically acceptable salt thereof.

2. The method of claim 1, wherein the eye cancer is uveal melanoma.

3. The method of claim 1, wherein ibudilast, or the pharmaceutically acceptable salt thereof, is administered for at least 3 months.

4. The method of claim 1, wherein ibudilast, or the pharmaceutically acceptable salt thereof, is administered for at least six months.

5. The method of claim 1, wherein ibudilast, or the pharmaceutically acceptable salt thereof, is administered for at least one year.

6. The method of claim 1, wherein ibudilast, or the pharmaceutically acceptable salt thereof, is administered for at least two years.

7. The method of claim 1, wherein ibudilast, or the pharmaceutically acceptable salt thereof, is administered at least once daily.

8. The method of claim 1, wherein ibudilast, or the pharmaceutically acceptable salt thereof, is administered orally.

9. The method of claim 1, wherein the therapeutically effective amount of ibudilast, or the pharmaceutically acceptable salt thereof, is from 0.1 mg to 720 mg per day.

10. The method of claim 1, wherein the therapeutically effective amount of ibudilast, or the pharmaceutically acceptable salt thereof, is at least 30 mg/day.

11. The method of claim 1, wherein the therapeutically effective amount of ibudilast, or the pharmaceutically acceptable salt thereof, is from 30 mg to 200 mg per day.

12. The method of claim 1, wherein the therapeutically effective amount of ibudilast, or the pharmaceutically acceptable salt thereof, is 60 mg to 600 mg daily.

13. The method of claim 1, wherein the therapeutically effective amount of ibudilast, or the pharmaceutically acceptable salt thereof, is 100 mg to 480 mg daily.

14. The method of claim 1, wherein the therapeutically effective amount of ibudilast, or the pharmaceutically acceptable salt thereof, is selected from the group consisting of 30 mg/day, 60 mg/day, 90 mg/day, 100 mg/day, 120 mg/day, 150 mg/day, 180 mg/day, 210 mg/day, 240 mg/day, 270 mg/day, 300 mg/day, 360 mg/day, 400 mg/day, 440 mg/day, 480 mg/day, 520 mg/day, 580 mg/day, 600 mg/day, 620 mg/day, 640 mg/day, 680 mg/day, and 720 mg/day.

15. The method of claim 1, wherein the therapeutically effective amount is administered as a single dose or is divided into two, three, or four doses.

16. The method of claim 1, wherein ibudilast is administered continually.

* * * * *